United States Patent [19]

Devos et al.

[11] Patent Number: 4,846,139

[45] Date of Patent: * Jul. 11, 1989

[54] PROCESS FOR THE PREPARATION OF CRYSTALLINE MALTITOL

[75] Inventors: Francis Devos, Hazebruuck; Pierre-Antoine Gouy, Lambersart, both of France

[73] Assignee: Roquette Freres, Lestrem, France

[*] Notice: The portion of the term of this patent subsequent to Jul. 18, 2006 has been disclaimed.

[21] Appl. No.: 143,275

[22] Filed: Jan. 6, 1988

Related U.S. Application Data

[63] Continuation of Ser. No. 810,246, Dec. 18, 1985, abandoned.

[30] Foreign Application Priority Data

Dec. 20, 1984 [FR] France ................. 84 19600

[51] Int. Cl.$^4$ .................. C13K 1/08; C13K 13/00; C07C 27/00
[52] U.S. Cl. .................. 127/40; 127/46.1; 127/46.2; 127/46.3; 127/58; 127/36; 127/38; 568/872; 568/863
[58] Field of Search ............... 127/46.2, 46.3, 38, 127/40, 58, 46.1; 568/863, 872

[56] References Cited

U.S. PATENT DOCUMENTS

| | | | |
|---|---|---|---|
| 3,708,396 | 1/1973 | Mitsuhashi et al. | 568/863 |
| 4,346,116 | 8/1982 | Verwaerde et al. | 426/548 |
| 4,408,041 | 10/1983 | Hirao et al. | 426/660 |
| 4,445,938 | 5/1984 | Verwaerde et al. | 568/863 |
| 4,487,198 | 12/1984 | Miyake et al. | 127/46.3 |

FOREIGN PATENT DOCUMENTS

| | | | |
|---|---|---|---|
| 0072080 | 2/1983 | European Pat. Off. | |
| 2826120 | 12/1979 | Fed. Rep. of Germany | 568/872 |
| 2000580 | 9/1969 | France | |
| 2499576 | 8/1982 | France | |
| 1283571 | 7/1972 | United Kingdom | |

OTHER PUBLICATIONS

Patents Abstract of Japan, vol. 9, No. 12 (C-261) [1735], 18 Janvier 1985, p. 96 C 261; and JP-A-59 162 953 (Showa Denko K.K.) 13-09-84.

Chemical Abstracts, vol. 98, No. 22, mai 1983, p. 105, No. 181481z, Columbus, Ohio, US; & JP-A-57 209 000 (Japan Organo Co., Ltd.) 22-12-1982.

*Methods in Carbohydrate Chemistry,* Whistler, vol. I. 1962, "Purification of Commercial Maltose", by M. L. Wolfrom and A. Thompson, pp. 334–339.

*Hydrolysis of the Amylopectins,* vol. 25, Jan. 1948, "Hydrolysis of the Amylopectins from Various Starches with Beta-Amylase", by J. E. Hodge et al., pp. 19–30.

Primary Examiner—Patrick P. Garvin
Assistant Examiner—Chung K. Pak
Attorney, Agent, or Firm—Larson and Taylor

[57] ABSTRACT

Process for the preparation of crystalline maltitol comprising successively:

catalytic hydrogenation of a saccharified starch milk in a vessel 203, a step of chromatographic fractionation of the hydrogenated syrup in a vessel 204, crystallation and separation of the maltitol crystals in vessels 206 and 207 and recycling through a pipe 309 emerging from the vessel 207 of the crystallization mother-liquors to the head of the chromatographic fractionation step.

3 Claims, 2 Drawing Sheets

PROCESS FOR THE PREPARATION OF CRYSTALLINE MALTITOL

This application is a continuation of application Ser. No. 810,246, filed Dec. 18, 1985, now abandoned.

The invention relates to a process for the preparation of crystalline maltitol.

Maltitol or α-D-glucopyranosyl 4-D-sorbitol is the result of hydrogenation of maltose.

It is known to prepare anhydrous crystalline maltitol by inducing the crystallization of said maltitol in a syrup sufficiently rich in this product and sufficiently purified (French Pat. No. 2,499,576).

Such a syrup is usually obtained by hydrogenation of syrup rich in maltose or by hydrogenation of crystalline maltose. It is important, in this process for the material subjected to hydrogenation to contain the maltose in a very high proportion so as to obtain, after said hydrogenation, only very little impurities of the polyalcohol type of a glucidic nature, which interfere with or even prevent the crystallization of the maltitol and render at the very least delicate the extraction of this maltitol from syrups which contain it.

Numerous processes are known for the manufacture of maltose-rich syrups, namely particularly:

that described by HODGE et Coll. in "Cereal Chemistry" no. 25, pages 19-30, January 1948, and which comprises a step of precipitation of the limit dextrins by alcoholic solutions, that described by WOLFROM and THOMPSON in "Methods in carbohydrate chemistry's, 1962, pages 334-335 and which comprises a repeated crystallization step of the maltose octaacetate followed by crystallization of the maltose, that described in U.S. Pat. No. 4,294,623 of MEIJI SEIKA granted 13.10.1981 and which comprises an absorption step on charcoal of the dextrins, that described in FR Pat. No. 2,510,581 of HAYASHIBARA filed 03.08.1982 and which comprises a step of chromatography on zeolites or cationic or anionic resins, that described in U.S. Pat. No. 4,429,122 of U.O.P. and which comprises an ultrafiltration step of the maltose syrups and, especially, that which is described in FR Pat. No. 2,012,831 of HAYASHIBARA filed 27.03.1979 and which comprises the combined use of several different enzymes, namely an α-amylase, αβ-amylase and an isoamylase and/or pullulanase.

The process described in the last of the abovesaid documents is that used within the scope of the abovesaid FR Pat. No. 2,499,576 to arrive at a syrup sufficiently rich in maltose subsequently hydrogenated and then subjected to crystallization.

Although representing a certain advance with respect to the processes described in the other documents cited, the process which is the subject of French Pat. No. 2,499,576—which consists, in a first step, of preparing a syrup rich in maltose but in low dry matter content then, in a second step, of raising the dry matter content of this syrup—, still presents several drawbacks among which are particularly:

that of being of little efficiency by reason of the low content of dry matter of the starting material, in the neighborhood of 80 g/l, necessary to obtain the highest possible efficiency of hydrolysis of the enzymes at the time of saccharification and involving a considerable concentration of the maltose syrup obtained; the abovesaid inefficient nature is accentuated by the inevitable loses of malitol in the crystallization liquors which contain non-negligible amounts thereof, that of involving inopportune retrogradation of the amylose, disturbing for saccharification and purification operations and due to the fact that the liquefaction must be carried out at very low values of dextrose-equivalent or DE.

It is therefore a particular object of the invention to overcome these drawbacks and to provide a process of the type concerned responding better to the various desiderata of practice than those hitherto existing.

Now, it happens that Applicants have succeeded in developing a novel industrial process providing easily and in excellent yield, crystaline maltitol of a richness in maltitol higher than 96% and, preferably, higher than 97%.

The process according to the invention comprises successively:

preferably an enzymatic saccharification step of a starch milk liquified by acid or enzymatic treatment and having a dry matter content of 25 to 45%, the parameters of enzymatic saccharification (type and amount of enzymes, temperature, duration of action and the like) being selected such that the maltose content of the syrup obtained is from 50 to 80% and, preferably, from 60 to 80% by weight on the dry matter, a catalytic hydrogenation step performed in a manner known in itself, a step of chromatographic fractionation of the maltitol syrup, which parameters are selected so that a fraction (A) rich in maltitol is obtained having the following composition, the percentages being expressed by weight to dry matter:

at least 87%, preferably from 87 to 97.5% and still more preferably from 87 to 95.5% of maltitol, a proportion of polyols of degree of polymerization or $DP \geq 4$ less than 1%, preferably less than 0.7% and, more preferably still, less than 0.6%, the complement to 100% being constituted by sorbitol and maltotriitol, a step of concentration of the fraction (A) rich in maltitol to a dry matter content suitable for permitting the formation of maltitol crystals and generally comprised between 75 and 92%, a step of crystallization and separation of the maltitol crystals and a step of recycling the crystallization mother-liquors to the head of the chromatographic fractionation step, this recycling of the crystallization mother-liquors enabling an almost quantitative extraction of the maltitol formed during the hydrogenation step of the maltose syrup.

The effectiveness of the chromatographic fractionation step enables the exclusion from the maltitol fraction of practically the totality of the hydrogenated products having a DP (degree of polymerization) higher or equal to 4, even if the syrups submitted to the fractionation contain notable proportions of the products, comprised for example between 5 and 40%. It becomes consequently possible to utilize hydrogenated starch hydrolysates whose richness in maltose is only 50%. Now, to prepare such syrups, it is possible to utilize starch milks having high dry matter contents, in any case comprised between 25 to 45%, situated about 40% like those which are generally utilized in glucoseries and dextroseries.

Due to the process according to the invention, the volumes to be treated are much less than in prior processes, the energy necessary for the evaporation of the water is found to be much reduced, the liquefaction of the starch can be done to a DE (Dextrose-Equivalent) higher than 2, compatible with an absence of retrogradation of the starch, the employment of enzymes like isoamylase or pullulanase can be avoided, the high osmotic pressures occasioned by the high concentration of the syrups employed protect these from any microbial contamination.

Figure 1:
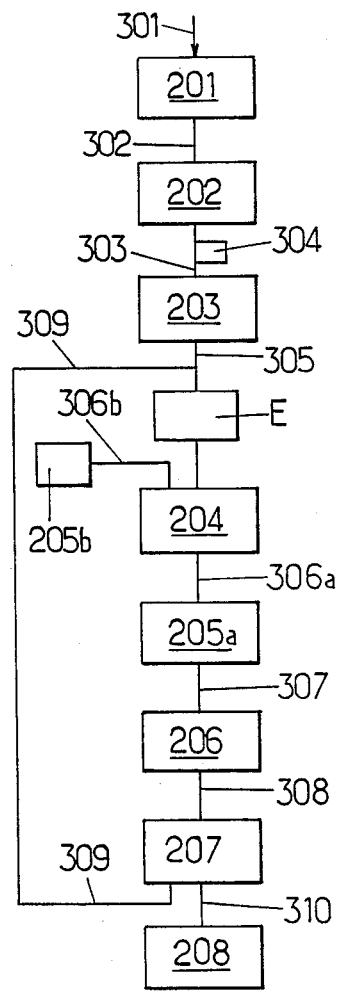
FIG. 1 is a diagrammatic flow sheet illustrating apparatus for carrying out a method in accordance with the invention.

The process according to the invention may be carried out by means of the installation shown diagrammatically in FIG. 1 and which comprises:

a vessel 201 within the liquefaction of the starch takes place, a vessel 202 within which the saccharification of the starch takes place, a vessel 203 within which the catalytic hydrogenation takes place, a concentration device E, a chromatographic separation vessel 204, one or several vessels 205a, 205b . . . , enabling concentration to the dry matter contents desired, alternatively or each continuously, the various fractions emerging from the chromatography and particularly the fraction rich in maltitol being collected at the vessel 205a, a vessel 207 enabling the separation of the crystals formed from their mother-liquors to be carried out, a vessel 208 enabling the drying of the crystals extracted from the vessel 207 to be performed.

The vessel 201 is supplied through a pipe 301 with starch or fecula milk with acid in the case of an acid liquefaction or with an α-amylase in the case of an enzymatic liquefaction under the conditions of temperature, of pH, of enzyme and of calcium ratio, known to the man skilled in the art, in order to obtain a DE (Dextrose-Equivalent) equal or higher than 2.

The vessel 202 is supplied through a pipe 302 with liquefied starch syrup emerging from the vessel 201. Before its entry into the vessel 202, there is added to the syrup emerging from the vessel 201, a malt β-amylase and the parameters of the saccharification are selected so that there is obtained a richness of maltose of at least 50% and, preferably, of at least 60% at the outlet of the vessel 202. The parameters of the enzymatic saccharification are especially the amount of enzyme utilized, the temperature, the pH and the duration of the amylolysis.

The vessel 203 is supplied from the vessel 202 through a pipe 303 with saccharified syrup, filtered and demineralized in a device 304 placed in the pipe 303. In the vessel 203, the catalytic hydrogenation of the maltose syrup is performed under conditions well known to the man skilled in the art, particularly with ruthenium or Raney nickel catalysts.

Preferably, the hydrogenation step is carried out with a Raney nickel catalyst, at hydrogen pressure higher than 20 kg/cm$^2$, preferably comprised between 40 and 70 kg/cm$^2$ and at a temperature of about 100° to 150° C. The hydrogenation is carried out until the content in reducing sugars of the hydrogenated syrup is lower than %, preferably lower than 1% and still more preferably lower than 0.5% (the content in reducing sugars being defined in weight of dextrose equivalent with respect to the dry matter).

The vessel 204 is supplied from the concentration device of evaporator E receiving through a pipe 305 the purified hydrogenated syrup emerging from the vessel 203. The pipe 305 also receives a pipe 309 coming from the vessel 207.

As indicated above, in the vessel 204 chromatographic fractionation of the maltitol syrup coming from the vessel 203 is performed.

The fractions emerging from the vessel 204 are routed respectively to the vessels 205a, 205b and through the pipes 306a, 306b. . . .

The fraction very rich in maltitol is led to the vessel 205a.

The step of chromatographic fractionation may be carried out in any manner known in itself, batch-wise or continuously (simulated mobile bed), on adsorbents of the highly acid cationic resin type, charged with alkali or alkaline-earth ions or again of the zeolite type charged with ammonium, sodium, potassium, calcium, barium, strontium, etc. ions.

Examples of such chromatographic separation processes are given in U.S. Pat. Nos. 3,044,904, 3,416,961, 3,692,582, FR No. 2,391,754, FR No. 2,099,336, U.S. Pat. Nos. 2,985,589, 4,024,331, 4,226,977, 4,293,346, 4,157,267, 4,182,633, 4,332,633, 4,405,445, 4,412,866 and 4,422,881.

According to a preferred embodiment, the separation step is carried out by employing the process and apparatus described in U.S. Pat. No. 4,422,811 and its corresponding French Pat. No. 79 10563 which Applicant Company owns.

Whatever the chromatographic separation process taken, recourse is had preferably, as adsorbent, to a strongly cationic resin placed in the calcium form and havig a proportion of divinylbenzene from about 4 to 10%.

The selection of the parameters of the chromatographic step, namely:

the elution rate, the rate of feeding with hydrogenated syrup, the rate of extraction of the fraction which is rich in maltitol, the composition of the zones of desorption, adsorbtion and enrichment, is explained and illustrated in the example.

The process thus described enables maltitol syrups (A) having a richness at least equal to 87% of maltitol and containing less than 1% of substances of degree of polymerization higher than or equal to 4, to be obtained. They are, more precisely, the percentages being expressed by weight on dry matter, composed of:

at least 87%, preferably from 87 to 97.5% and still more preferably from 87 to 95.5% of maltitol, a proportion less than 1%, preferably less than 0.7% and, more preferably still, less than 0.6% of polyols of degree of polymerization higher than or equel to 4, the complement to 100% being constituted by sorbitol and maltotriitol, preferably a proportion of sorbitol less than 5% and, more preferably still, less than 2%, a content of maltotriitol generally comprised between 2.5 and 13% by weight.

This process leads also to the concomitant production of a syrup enriched in maltotriitol and to that of a syrup composed of hydrogenated products of high molecular weight.

These two types of syrup are extracted from the chromatography vessel through the pipe 306b.

As indicated aove, the vessel 205a is supplied with syrup very rich in maltitol (A) coming from the chromatography vessel through the pipe 306a. This vessel 205a is arranged so as to permit the concentration of the maltitol rich syrup. Preferably, this concentration is continued until obtention of a dry matter content comprised between 75 and 92%. This concentration can be carried out continuously and, preferably, under reduced pressure. During this step, it is possible to initiate or not the formation of the crystals. It is in any case designated to carry to at least 80% of the content of total dry matter of the maltitol syrup.

The vessel 206 is arranged so as to permit the initiation of crystallization to be achieved in the vessel 205a or to permit this crystallization to be carried out completely.

It is normally provided with devices enabling this operation to be well carried out, namely stirring and cooling means for the crystalline mass, which means can be employed in various ways but in any case such that the crystalline masses are cooled in controlled and homogeneous manner.

It is connected to the vessel 205a through pipe 307, a pipe 308 enabling the crystalline masses to be led to the vessel 207.

The vessel 207 generally comprises a device with centrifugal action adapted to separate crystals from their mother-liquors and provided with a device for washing said crystals so as to bring them to a sufficient chemical purity.

The removal of the mother-liquors is effected through a pipe 309 which brings back said mother-liquors to the pipe 305, immediately downstream of the hydrogenation vessel 203.

It is through a pipe 310 that the crystals isolated in the vessel 207 are led to the vessel 208.

The vessel 208 comprises drying means enabling the residual moisture to be removed from the crystals: it may be static or pneumatic devices operating under positive or negative pressure: it is preferably of the type with a current of hot air carrying or maintaining said crystals in suspension.

These crystals are obtained easily in a practically anhydrous form (water content less than 0.5%); they constitute a non-hygroscopic powder, flowing quite freely.

The mother-liquors from the crystallization of the maltitol are reincorporated preferentially before the step of concentration in the flow of syrup emerging from the hydrogenation vessel 203. The resulting mixture is brought into the device E to a concentration enabling normal and economic operation of the chromatographic fractionation installation.

The process according to the invention enables, due to the recycling of the mother-liquors, the extraction with an efficiency never yet achieved and in its crystalline form of almost the whole of the maltitol present in a maltitol syrup.

The invention will be still better understood by means of the example relating to an advantageous embodiment of the invention without limiting the scope thereof.

EXAMPLE

An installation such as that shown in FIG. 1 is resorted to.

A starch milk from wheat with a dry matter content of 37%, is liquefied in the vessel 201 at a pH of 6.3, at a temperature of 108° C. and with an addition of $0.3°/_{oo}$ of liquefying enzyme of the type marketed by the NOVO Company under the trademark "THERMAMYL". At the outlet of the liquefaction installation, a thermal shock of 10 seconds at 130° C. is applied. The DE at the liquefaction outlet was equal to 5.0.

The pH is adjusted at the outlet of the liquefaction installation to a value of 5.5 and $0.55°/_{oo}$ of malt $\beta$-amylase marketed by the Company FINNSUGAR under the name "SPEZYME BBA 1500" is added.

The saccharification is carried out in the vessel 202 at this pH for 48 hours at 57° C.

At the end of saccharification, the analysis by liquid chromatography shows the presence of:
Dextrose: 2.3% by weight
Maltose: 61.3% by weight
Trisaccharides: 7.5% by weight
Products of DP 4 to DP 10: 6.2% by weight
Product of DP>10: 22.7% by weight.

The hydrogenation is carried out in vessel 203 (the parameters being those described above), followed by a purification and a concentration in the device E; a syrup rich in maltitol is obtained whose composition is as follows:
Sorbitol: 3.3% by weight
Maltitol: 60.4% by weight
Trisaccharides: 9.2% by weight
Products of DP 4 to DP 10: 7.0% by weight
Product of DP>10: 20.1% by weight.

Fractionation of this hydrolysate rich in hydrogenated maltose follows in the installation 204 for continuous chromatographic separation whose constructional and operational details are those described in U.S. Pat. No. 4,422,881 and in the corresponding French Pat. No. 79 10563, these details only being repeated here to the extent that comprehension of the text requires it.

Figure 2:
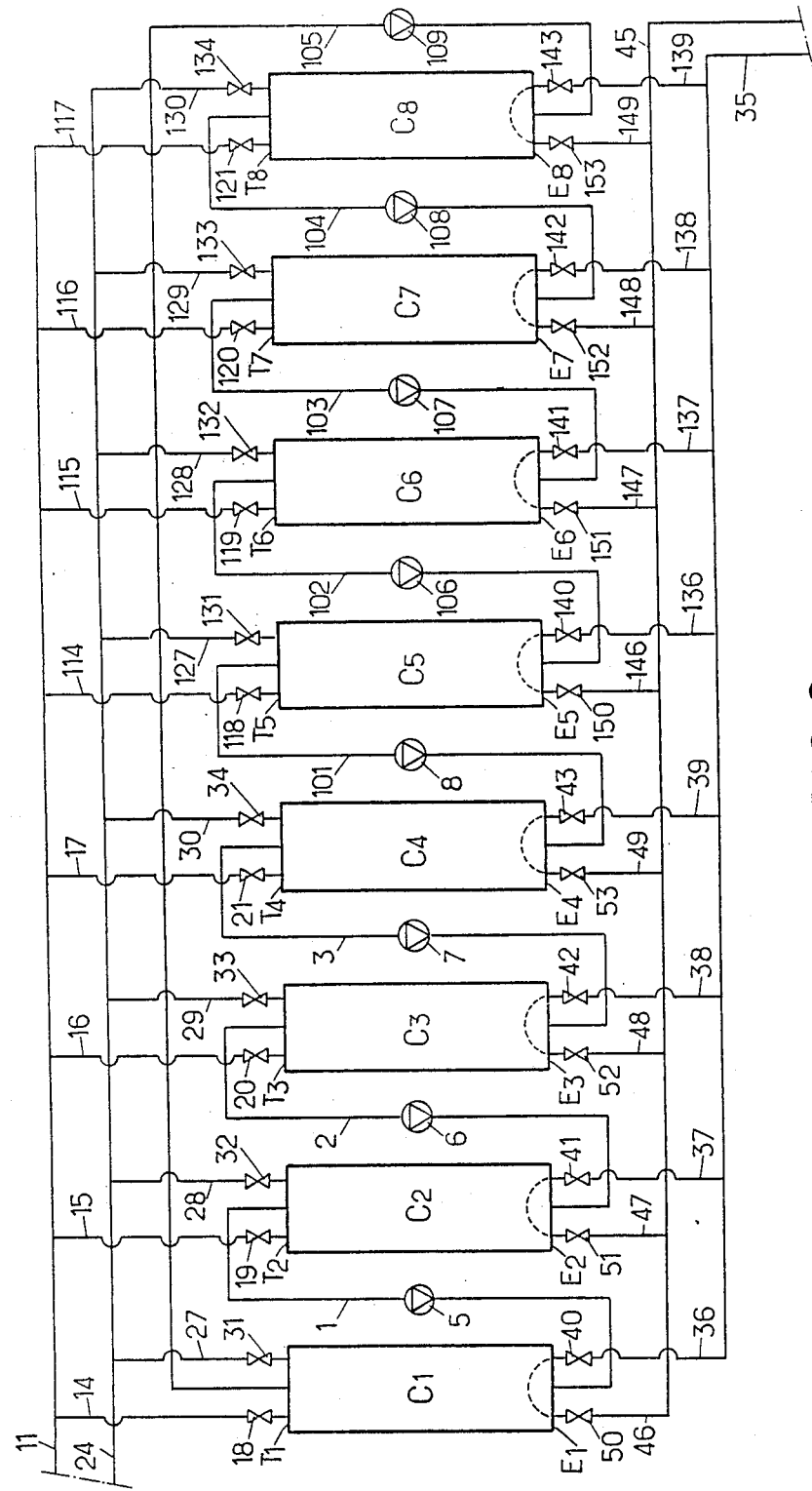
FIG. 2 is a diagrammatic view of apparatus suitable for carrying out a chromatographic fractionation step in a method in accordance with the invention.

This installation 204 comprises, as shown in FIG. 2 of the American patent (taken again here as FIG. 2, for the detailed explanation of which reference will be made to the American patent), eight columns or stages $C_1$ to $C_8$ of 200 liters each, filled with adsorbent of the strong cationic resin type in the calcium form and of fine granulometry (0.2 to 0.4 millimeters).

Figure 3:
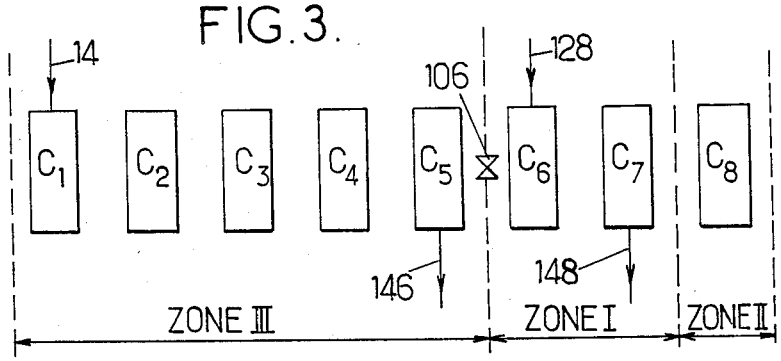
FIG. 3 is a generalized diagrammatic flow sheet representing the apparatus of FIG. 2.

By calibration of the electrovalves, there is established in this installation a desorption zone I of two stages, a desorption zone II of one stage and a zone III of enrichment and separation of the hydrogenated limit dextrins and of the maltotriitol, of five stages as shown in FIG. 3 which is a diagrammatic representation of the installation according to FIG. 2 and in which there is only shown:
the columns $C_1$ to $C_8$,
the closing device, i.e. the electrovalve 106,
the pipes for supply of maltitol syrup to be fractionated and of water, shown respectively at 14 (corresponding to the pipe 305, FIG. 1) and 128 and the pipe 148 for extraction of the maltitol enriched syrup on the one hand, and the pipe 146 for the extraction successively of sorbitol, of limiting dextrins and of maltotriitol, on the other hand.

The closure device 106 (particularly an electrovalve) maintains in the configuration adopted, a total fluid-tightness between, on the one hand, the zone III, which is an enrichment zone at the end of which are therefore recovered successively reliquate of strongly adsorbed sorbitol, the hydrogenated limiting dextrins, then the fraction enriched in maltotriitol and, on the other hand, the zone I of desorption of the maltitol, at the head of which zone is introduced the desorption water.

This closure device ensures the direction of passage of the liquid phase on the selective adsorbent and avoids particularly contamination of the maltitol enriched by traces of hydrogenated limiting dextrins of high molecular weight, whose speed of migration within the resin is largely superior to that of the maltitol.

A timer adjusted to 23'30" ensures for the flow rate indicated below a supply of water sufficient to effect desorption of the totality of the maltitol at the first stage of first column of the desorption zone I, and a supply of a volume of hydrogenated starch hydrolyzate ich in maltitol compatible with the volume of adsorbent and its adsorption capacity, so as to obtain a ratio of extraction of maltitol at least equal to 90% of the maltitol present in the hydrogenated hydrolyzate and this to a richness at least equal to 87% of true maltitol. The syrup obtained has a content less than 0.5% of products of DP higher than or equal to 4.

The above-said ratios of extraction and purity are kept constant by adjusting the flow rate of the extraction pump (not shown) of the adsorbed maltitol. The output of the "hydrogenated limiting dextrins" and "enriched maltotriitol" fractions is effected at atmospheric pressure and its constant flow rate results from the difference between the supply flow rates and the extraction flow rates.

The hydrogenated starch hydrolyzate rich in maltitol which is introduced into the installation at the head of the enrichment zone III, shows, as indicated above a content of dry matter of 51.5%. The temperature within the separation columns is kept at about 90° C.

Figure 4:
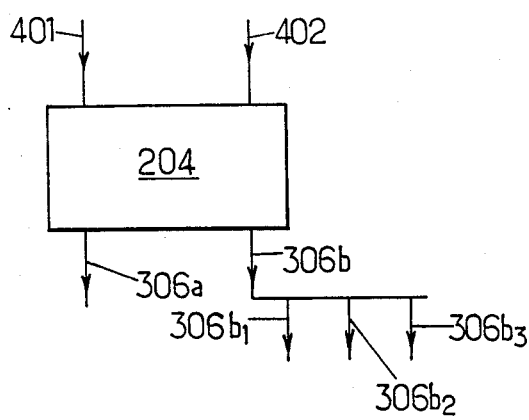
FIG. 4 is a diagrammatic flow sheet of a chromatography apparatus for carrying out a method in accordance with the invention.

FIG. 4 shows diagramatically at 204 the installation of FIGS. 2 and 3, the same reference numerals denoting the same elements for the parts in common in FIG. 1. The chromatography installation 204 includes a pipe 306b through which the excess water containing a large fraction of sorbitol and the hydrogenated limiting dextrin fraction with a molecular weight higher than or equal to DP 4, are removed; these extracts are of low dry matter content and exit through the pipes 306b$_1$ and 306b$_2$.

The supply of water is effected through a pipe 402.

The arrows applied to the pipes indicate the direction of flow.

The chromatography unit 204 operates as follows:

the hydrogenated starch hydrolyzate which has to be subjected to chromatographic fractionation is led through the pipe 401 at a flow rate of 90 liters/hour and has a dry matter content of 51.5%, the water is introduced through the pipe 402, with a flow rate of 430 liters/hour, the enriched maltitol free from hydrogenated limiting dextrins is recovered through the pipe 306a with a flow rate of 145 liters/hour, its average dry matter content being 23%, the total amount of liquids is extracted from the installation with a total flow rate of 375 liters/hour, being composed successively:

of an excess water fraction, extracted through the pipe 306b$_1$, containing at low concentration and high purity, sorbitol and of a fraction at low concentration and of high richness in hydrogenated limiting dextrins at DP higher than or equal to 4 extracted through the pipe 306b$_2$, the whole representing an equivalent of 305 liters/hour, the content of dry matter being 4.1%; these fractions correspond to the 18.5 first minutes of the cycle, of a fraction of enriched maltotriitol, of an equivalent of 70 liters/hour led through a pipe 306b$_3$ to a purification installation (not shown), the dry matter content of this fraction being 8.2%; this fraction corresponds to the five last minutes of the cycle.

Tables I and II below summarize the conditions characterizing the operation of the chromatographic fractionation installation.

TABLE I

|  | Maltitol syrup | Water | Total |
| --- | --- | --- | --- |
| Flow rate | 90 l/h | 430 l/h | 520 l/h |
| Density | 1.25 kg/l | | |
| Dry matter | 51.5% | | |
| Mass flow rate | 56.3 kg/h | | 56.9 kg/h |
| Richness in maltitol | 60.4% | | |
| Mass flow rate of maltitol | 34 kg/h | | 34 kg/h |

The effluents extracted from the installation are identified in Table II.

TABLE II

|  | Enriched Maltitol | Sorbitol then hydrogenated limiting dextrins | Maltotriitol | Total |
| --- | --- | --- | --- | --- |
| Flow rate | 145 l/h | 305 l/h | 70 l/h | 520 l/h |
| Density | 1.11 kg/l | 1.02 Kg/l | 1.03 kg/l | |
| Dry matter | 23% | 4.5% | 8.2% | |
| Mass flow rate | 37 kg/h | 14.0 kg/h | 5.9 kg/h | 56.9 kg/h |
| Richness in maltitol | 90.5% | 2% | 3.9% | |
| Mass flow rate in maltitol | 33.5 kg/h | 0.28 kg/h | 0.23 kg/h | 34.1 kg/h |

This result corresponds to a ratio of extraction by weight of:

37/56.3 = 67% of enriched maltitol syrup at 90.5% and 33.5/34 = 98.5% extraction of the maltitol Analysis of the enriched maltitol fraction gives the following results:

Sorbitol: 1.3% by weight
Maltitol: 90.5% by weight
DP 3: 7.8% by weight
DP $\geq$ 4: 0.4% by weight.

Analysis of the enriched maltotriitol syrup fraction gives the following results:

Sorbitol: 0.4% by weight
Maltitol: 3.9% by weight
Maltotriitol: 51% by weight
Maltotetraitol: 10.6% by weight
Products of DP equal to 5: 9.5% by weight
Products of DP > 5: 24.6% by weight.

It may be observed, from these various measurements that it was possible, by this process of fractionation from a standard syrup obtained by saccharification with β-amylase alone and at the high customary concentrations, to extract a proportion of 98.5% of the maltitol at a richness of 90.5%.

The maltitol syrup obtained is characterized by the almost total absence of hydrogenated polymers of glucose of $DP \geq 4$.

It was possible to extract conjointly a syrup enriched in maltotriitol at a richness of 51%.

In the vessel 205a, under a reduced pressure the fraction rich in maltitol was concentraed to a content of 90% of dry matter at a temperature of 80° C. This syrup was collected in the crystallization vessel which is provided with a double jacket. After four hours of maintenance at the temperature of 75° C., a start of very regular crystallization is seen to appear (spontaneous nucleation).

Cooling of the crystallization vessel then followed at a speed of 1° C./hour from 75° C. to 25° C. in 50 hours.

The crystalline masses obtained were drained under the following conditions:

| | |
|---|---|
| weight of cystalline mass with 90% of dry matter | 102.2 kg |
| amount of clearing water | 45 liters |
| total duration of a cycle (including the periods of acceleration, of retardation and of consolidation of the cake) | 30 minutes. |

The average results obtained were established as follows (average for 10 cycles of drainage):

| | |
|---|---|
| average weight of moist crystals | 63.2 kg |
| moistness of the crystals | 5.4% |
| richness of the crystals | |
| in maltitol | 99% |
| in sorbitol | 0.5% |
| richness of the mother-liquors | |
| in maltitol | 75% |
| in sorbitol | 5.6% |
| in maltotriitol | 19.5% |
| in products of $DP \geq 4$ | 0.9% |
| average dry matter of the mother-liquors | 38.4% |
| average mass of mother-liquors | 83.8 kg |
| average yield of crystallization (anhydrous crystalline maltitol with respect to the total dry matter subjected to crystallization). | 65% |

The recycling phase of the crystallization mother-liquors provided according to the invention, starts after 48 hours of operation of the chromatographic fractionation device in the aforesaid conditions.

The crystallization mother-liquors accumulated during 48 hours are recycled through the pipe 309 immediately upstream of the evaporation vessel E of the maltitol syrup supplying the chromatographic installation 204.

The recycling was done at the rate of 100 kg of dry matter of mother-liquors per 330 kg of dry matter of maltitol syrup at 60.4% richness emerging from the hydrogenation step, namely 23% approximately of the dry matter of the syrup supplying the chromatography device.

This percentage corresponds to a state of equlibrium of the process.

Under these conditions, the whole of the mother-liquors obtained at the crystallization step again is subjected to the chromatographic fractionation.

The composition of the syrup supplying the chromatography step has only been slightly modified, since it is established at:

sorbitol: 3.8%
maltitol: 63.8%
maltotriitol: 11.4%
$DP \geq 4$: 21%.

The richness in maltitol of the supply has therefore not appreciably changed, at the most there may be observed a slight increase in the content of sorbitol and maltotriitol accompanied by a co-relative reduction in the hydrogenated products of high molecular weight ($DP \geq 4$).

The chromatographic fractionation installation operated under the supply conditions of water and of syrup, and under the extraction conditions of maltitol syrup and the like with the flow rates mentioned in Tables I and II above.

After 24 hours of operation, equilibrium being reached, the maltitol effluent showed the following composition:

sorbitol: 1.9%
maltitol: 90.5%
DP 3: 7.4%
$DP \geq 4$: 0.2%.

The concentration and then the crystallization of this syrup under the conditions already described again supplied, after draining, crystalline maltitol with a yield of 65% with respect to the total dry matter subjected to crystallization.

These crystals were dried on a fluidized bed dryer. They showed the following characteristics:

TABLE III

| | |
|---|---|
| $H_2O$ | 0.3% |
| rotatory power (10% aqueous solution) at 20° C. D line of sodium | 106° |
| *melting temperature at the peak | 150.6° C. |
| richness by high pressure liquid chromatography | 98.5% |

*thermal characteristic read on the D.S.C. SETARAM 111, apparatus, 50 mg of substance, heating speed 2° C./min.

They are non-hydroscopic and form a powder which flows freely.

It results from the foregoing that the process according to the invention for manufacturing crystalline maltitol enables an almost total extraction of the maltitol formed in the hydrogenation steps since the crystallization mother-liquors can be totally recycled and since the only loss of maltitol takes place in the chromatography step where only a very small fraction of the latter is mixed with the portion rich in maltotriitol as well as with the other enriched fractions which it is possible to separate. Now, at this level, the extraction yields of the maltitol are practically quantitative since 98.5% of the maltitol present in the feed syrup of the chromatographic fractionation system is again found in the fraction enriched in maltitol subjected to crystallization.

Thus therefore, by this novel process, almost the totality of the maltose formed in an enzymatic hydrolysis of starch can be rendered of value by extraction in the form of highly pure crystalline maltitol.

As is self-evident and as emerges besides already from the foregoing, the invention is in no way limited to those of its types of application and embodiments which have been more especially envisaged; it encompasses, on the contrary, all modifications.

We claim:

1. Process for the preparation of maltitol, comprising the successive steps (a) to (g) of:
   (a) liquefying starch milk having a dry matter content of 25 to 45% by weight to a dextrose-equivalent from higher than 2 to about 25,
   (b) subjecting the liquefied starch to the action of an enzyme proper to saccharify said starch until a maltose syrup having a dry matter content of 25 to 45% by weight and containing from 50 to 80% of maltose by weight of the dry matter is obtained,
   (c) catalytically hydrogenating said maltose syrup with Ruthenium or Raney nickel catalysts to provide a maltitol syrup containing maltitol in a proportion from 50 to 80% by weight based on the dry matter, sorbitol, maltotriitol and polyols of degree of polymerization $\geq 4$,
   (d) submitting said maltitol syrup to a chromatographic fractionation, the process conditions of which are selected in order to obtain a fraction (A) rich in maltitol comprising
      at least 87% by weight of maltitol based on the dry matter of the fraction,
      a proportion less than 1% by weight based on the dry matter of the fraction of polyols of a degree of polymerization $\geq 4$,
      the remainder being sorbitol and maltotriitol,
   (e) concentrating the fraction (A) to a dry matter content comprised between 75 and 92% by weight suitable for permitting the formation of maltitol crystals,
   (f) crystallizing the maltitol from the concentrated fraction (A), providing maltitol crystals and mother-liquors, said maltitol crystals being separated from the mother-liquors,
   (g) recyling the mother-liquors to the chromatographic fractionation step (d).

2. Process according to claim 1, wherein the fraction (A) comprises from 87 to 97.5% by weight based on the dry matter of maltitol and a proportion of polyols of degree of polymerization $\geq 4$ less than 0.7% by weight based on the dry matter.

3. Process according to claim 1, wherein the fraction (A) comprises from 87 to 95.5% by weight based on the dry matter of maltitol and a proportion of polyols of degree of polymerization $\geq 4$ less than 0.6% by weight based on the dry matter.

* * * * *